United States Patent [19]

Zinn

[11] Patent Number: 5,409,677

[45] Date of Patent: Apr. 25, 1995

[54] PROCESS FOR SEPARATING A RADIONUCLIDE FROM SOLUTION

[75] Inventor: Kurt R. Zinn, Columbia, Mo.

[73] Assignee: The Curators of the University of Missouri, Columbia, Mo.

[21] Appl. No.: 112,765

[22] Filed: Aug. 26, 1993

[51] Int. Cl.$^6$ ............................................. C01F 1/00
[52] U.S. Cl. ....................................... 423/2; 423/21.5; 423/24
[58] Field of Search ............................ 423/2, 24, 21.5

[56] References Cited

U.S. PATENT DOCUMENTS

| | | | |
|---|---|---|---|
| 3,957,945 | 5/1976 | Grant et al. | 423/2 |
| 4,487,738 | 12/1984 | O'Brien, Jr. et al. | 376/192 |
| 4,563,256 | 1/1986 | Sudderth et al. | 204/108 |
| 4,756,904 | 7/1988 | Crook | 424/1.1 |
| 4,816,233 | 3/1989 | Rourke et al. | 423/21.5 |
| 4,898,719 | 2/1990 | Rourke et al. | 423/21.5 |
| 4,968,504 | 11/1990 | Rourke | 423/7 |
| 5,019,362 | 5/1991 | Rourke et al. | 425/21.5 |

OTHER PUBLICATIONS

Zinn et al., Antibody, Immunoconjugates, and Radiopharmaceuticals, vol. 5, No. 3, 1992; Sep. 11, 1992.
Zinn et al., J. Nucl. Medicine, Aug. 27, 1992.
Research Scale Chromatography (Bio Rad); pp. 97–108.
Bio Rad Chelex Instruction Manual; pp. 2–15.
1990 Bio Rad Price List; pp. 24–35.
1991 Bio Rad Price List; pp. 1–8.
Bhatki, et al., 63078x, Preparation of Carrier-free copper-64,67 nuclides by liquid-liquid extraction, Chemical Abstracts, vol. 70, 1969, p. 424.
Toth, et al., 136273f, Separation of carrier-free copper-64 and (or) copper-67 from reactor irradiated zinc by means of the spontaneous deposition of copper on platinum black; Nuclear Phenomena, vol. 73, 1970, p. 395.
Mirzadeh, et al., 118:68546t, Spontaneous electrochemical separation of carrier-free copper-64 and copper 67 from zinc targets, Nuclear Technology, vol. 118, 1993, p. 579.
Gelis, 34632a, Marcoaggregates of copper-64 and geletin, Pharmaceuticals, vol. 74, 1971, p. 207.
Gelis, 49974d, Gelatin copper-64 marcroaggregates, Chemical Abstracts, vol. 76, 1972, p. 278.
Gelis, 168660d, Colloidal cuprous Cu-64 oxide for liver scintigraphy, Pharmaceuticals, vol. 77, 1972, p. 271.
F. Dyer, et al., The Radiochemistry of Copper, Nat. Academy of Sciences, 1961.
Chikuma, et al., Chelate-Forming Resins Prepared by Modification of Anion-Exchange Resins, Talanta, 1980, vol. 27, pp. 807–810.
G. Schmuckler, An Analytical Approach to Chelating Resins, Talanta, 1963, vol. 10, pp. 745–751.
H. Loewenschuss, et al., Chelating Properties of the Chelating Ion Exchanger Dowex A-1, Talanta, 1964, vol. 11, pp. 1399–1408.
S. Mirzadeh, et al., Production of No-Carrier Added 67Cu, Appl. Radiat. Isot., vol. 37, No. 1, pp. 29–36, 1986.
K. Fritze, The Preparation of High Specific Activity Copper 64, Radiochimica Acta, 1964, p. 166.
G. Bormans, et al., A 62Zn/62Cu Generator for the Routeine Production of 62Cu-PTSM, Appl. Radiat. Isot., vol. 43, No. 12, pp. 1437–1441, 1992.

(List continued on next page.)

Primary Examiner—Ngoclan T. Mai
Attorney, Agent, or Firm—Senniger, Powers, Leavitt & Roedel

[57] ABSTRACT

A process for separating a radionuclide such as radioactive Cu-64 from a mixture containing the radionuclide and a precursor element from which the radionuclide is formed. A weak acid solution is prepared which contains the mixture of the radionuclide and the element. The solution is contacted with a ligand which preferentially forms a complex with the radionuclide relative to the precursor element. The radionuclide complexed to the ligand is separated from the precursor element and released from the ligand by contacting the ligand with an acid.

20 Claims, No Drawings

OTHER PUBLICATIONS

E. L. Hetherington, et al., The Preparation of High Specific Activity Copper-64 for Medical Diagnosis, Appl. Radiat. Isot., vol. 37, No. 12, pp. 1242–1243, 1986.

C. Mathias, et al., Evaluation of a Potential Generator-Produced PET Tracer for Cerebral Perfusion Imaging: Single-Pass Cerebral Extraction Measurements and Imaging with Radiolabeled Cu-PTSM, J. Nucl. Med. 1990, 31:351–359.

C. Anderson, et al., Copper-64-Labeled Antibodies for PET Imaging, J. Nucl. Med. Sep. 1992, 33:1685–1691.

K. Burger, Analytical Use of 1,3-Dimethyl-4-imino-5-oximinoalloxan-1, Talanta, 1961, vol. 8, pp. 77–84.

K. Brajter, et al., Preconcentration and Separation of Metal Ions by Means of Amerlite XAD-2 Loaded with Pyrocatechol Violet, Talanta, vol. 35, No. 1, pp. 65–67, 1988.

Y. Sakai, Photometric Determination of Copper with N-(Dithiocarboxy)Sarcosine After Preconcentration with Amberlite XAD-2 Resin, Talanta, 1980, vol. 27, pp. 1037–1076.

D. Ryan, Comparison of Chelating Agents Immobilized on Glass with Chelex 100 for Removal and Preconcentration of Trace Copper(II), Talanta, vol. 32, No. 9, pp. 859–863, 1985.

J. Adam, et al., Analytical Use of the Selective Extraction of Copper as its Phenylacetate, Talanta, 1972, vol. 19, pp. 1105–1111.

A. Reddy, et al., Sequential Extraction and Determination of Copper and Nickel with 2,4-Dihydroxyacetophenone Thiosemicarbazone, Talanta, vol. 33, No. 7, pp. 617–619, 1986.

M. Khuhawar, et al., High Performance Liquid Chromatographic Determination of Copper(II) and Nickel(II) by Using Solvent Extraction and Bis(Acetylpivalylmethane)Ethylenediimine as Complexing Reagent, Talanta, vol. 39, No. 6, pp. 609–612, 1992.

J. Hibbits, et al., The Analysis of Beryllium and Beryllium Oxide-II, Talanta, 1960, vol. 4, pp. 101–103.

The Merck Index, 10th Edition, 1983.

A. Dasgupta, et al., A New Separation Procedure for 67Cu from Proton Irradiated Zn, Appl. Radiat. Isot., vol. 42, No. 4, pp. 371–376, 1991.

Zinn, Fourth Conference on Radioimmunodetection and Radioimunotherapy of Cancer, Princeton, N.J., Sep. 16, 1992.

Zinn, Society of Nuclear Medicine Annual Meeting, Jun. 8–Jun. 11, 1993, Toronto, Canada.

PROCESS FOR SEPARATING A RADIONUCLIDE FROM SOLUTION

BACKGROUND OF THE INVENTION

This invention relates to a process for recovering a radionuclide by separating it from a solution containing the radionuclide and its precursor.

Radioisotopes are commonly used for research, treatment and diagnosis in the field of nuclear medicine. Such applications include, for example, liver, lung, bone and tumor scanning and radiotherapy. In particular, positron emission tomography (PET) is a procedure in the field of nuclear medicine which offers advantages for radioimmunodiagnosis of cancer. PET requires radionuclides of high specific activity and high purity. Radionuclides are also in widespread use in both research and testing laboratories. In a significant fraction of these applications the radio-purity, chemical purity and specific activity of the radionuclides are critical to the successful outcome of the specific applications. Therefore, methodologies of the type described in this invention are essential to keep pace with the medical, scientific and engineering technologies in which they are experiencing an expanding demand.

Among the radionuclides which have been proposed for such applications are copper-62, scandium-47, copper-64 and copper-67. Cu-62 has been generated by use of a cyclotron to produce Zn-62, which then decays to Cu-62. Enriched Ca-46 has been irradiated to form Ca-47, which then decays to Sc-47. Copper-64, which is of special interest for use in PET, has been produced from zinc by fast neutron reaction involving the bombardment of a zinc target (48% natural abundance of Zn-64) as disclosed in Fritze, "The Preparation of High Specific Activity Copper 64", Radiochimica Acta 1964, 3:166-67 and Mirzadeh et al., "Production of No-Carrier Added Cu-67", Appl. Radiot. Isot., Vol. 37, No. 1, pp. 29-36, (1986). High-energy, or fast neutrons, having energies of 1 MeV or greater, can induce nuclear reactions that result in the ejection of a proton from the nucleus when the neutron is captured. Since the masses of the neutron and proton are nearly the same, the nominal mass of the transmutated product nuclide remains constant. However, since the captured neutron carries no charge and the ejected proton carries a positive one charge, there is a net loss of one positive charge. Hence the target atom which captured the neutron and ejected the proton is transmutated to the adjacent element in the periodic table having the atomic number one less than the target element. The importance of this nuclear transmutation process, as it relates to radioisotope production of the type serviced by this invention, is that transmutation of Zn-64 atoms produces radioactive Cu-64 atoms exclusively. Hence practical methodologies, such as this invention, that provide the chemical technology to separate the radioactive Cu-64 from the non-radioactive Zn-64 provide the means by which high-specific-activity radioisotopes can be produced. Zn-64(n,p)Cu-64 is the shorthand characterization for a stable Zn-64 atom capturing a neutron and ejecting a proton to produce radioactive Cu-64. Other examples of nuclear transmutation caused by high-energy neutron capture with proton ejection that are relevant to this invention are Zn-67(n,p)Cu-67 and Ti-47(n,p)Sc-47.

Radionuclides produced by bombardment reactions and decay reactions must be separated from their precursor nuclides before they can be used for radiodiagnosis and radiotherapy. Such separation is difficult because a radionuclide product is typically in a mixture containing 10,000 or more times as much of the precursor as of the radionuclide product. Methods which have been employed for radionuclide separation of this type include solvent extraction, electrodeposition and ion exchange.

Solvent extraction methods have been complicated and typically produce volumes of liquid organic waste contaminated with the precursor. Due to the employment of strong chelating agents, solvent extraction methods can result in product solutions contaminated with extraneous metal ions from reagents and other sources. Separation by electrodeposition involves the use of an electrolytic cell for repeated deposition and dissolution of the radionuclide product, for example, copper, onto an electrode. It has been reported Mirzadeh et al., "Production of No-Carrier Added Cu-67" Appl. Radiat. Isot., Vol. 37, No. 1, pp. 29-36, (1986), however, that the dissolved copper containing product must be subjected to an additional separation technique because electrodeposition is not effective for separation from impurities which are more electropositive than copper. Prior anion exchange chromatographic methods have not been consistently successful in minimizing breakthrough, that is, contamination of the product with precursor nuclide. Another disadvantage of such methods is that they typically require ion exchange columns with relatively large bed volumes.

SUMMARY OF THE INVENTION

Among the several objects of the invention, therefore, are the provision of a novel method for the separation of a radionuclide from a mixture of the radionuclide and its precursor element; the provision of such a method which yields radionuclides suitable for use in industrial and nuclear medicine applications and, especially, for use in PET; the provision of such a method which yields radionuclides of high specific activity; the provision of such a method which produces radionuclides in high yield with a minimum of breakthrough contamination by precursors; the provision of such a method which does not employ metallic oxide columns which can potentially contaminate the daughter product solution; the provision of such a method which is less complicated, uses less space and materials, is faster, more economical and which produces less waste than previous separation techniques; the provision of such a method which does not collaterally produce large volumes of liquid waste; the provision of such a method which can be readily scaled up to commercial dimensions; the provision of such a method that is fully consistent with the radiation safety concept of ALARA (as low as reasonably achievable) which is required by nuclear regulatory agencies; the provision of such a method which is particularly suitable for the separation of Cu-62 from Zn-62, Cu-64 from Zn-64, Cu-67 from Zn-67, Sc-47 from Ti-47 and Sc-47 from Ca-47.

Briefly, therefore, the invention is directed to a process for separating a radionuclide from a mixture containing the radionuclide and a precursor element of the radionuclide in which the mass of the precursor element is at least about 100 times the mass of the radionuclide. A weak acid solution is prepared which contains the mixture of the radionuclide and the element. The solution is contacted with a ligand which preferentially forms a complex with the radionuclide relative to the precursor element, the percentage of the radionuclide which is complexed by the ligand, as a percentage of the total radionuclide in the mixture, being on the order of at least about 100 times the percentage of the precursor element which is complexed by the ligand, as a percentage of the total precursor element in the mixture. The radionuclide complexed to the ligand is separated from the precursor element and released from the ligand.

The invention is further directed to a process for separating a copper radionuclide from a mixture containing the copper radionuclide and a zinc precursor element of the copper radionuclide in which the mass of the zinc precursor element is at least about 100 times the mass of the copper radionuclide. A weak acid solution is prepared which contains the mixture of the copper radionuclide and the zinc precursor element. The solution is contacted with a ligand which preferentially forms a complex with the copper radionuclide relative to the zinc precursor element, the percentage of the radionuclide which is complexed by the ligand, as a percentage of the total radionuclide in the mixture, being on the order of at least about 100 times the percentage of the precursor element which is complexed by the ligand, as a percentage of the total precursor element in the mixture. The copper radionuclide complexed to the ligand is separated from the zinc precursor element and released from the ligand.

The invention is still further directed to a process for producing a radionuclide adapted for radiation therapy or diagnosis of a mammal by separating a copper radionuclide from a mixture of copper radionuclide and a zinc precursor element. A solution is formed in weak acid which contains the mixture of copper radionuclide and zinc precursor element, the copper radionuclide resulting from fast neutron capture by a zinc target and the solution having a pH in the range of about 2.3 to 3.1. The solution is contacted with a ligand immobilized on a resin, which ligand preferentially forms a complex with the copper radionuclide relative to the zinc precursor element. The percentage of the radionuclide which is complexed by the ligand, as a percentage of the total radionuclide in the mixture, is on the order of at least about 100 times the percentage of the precursor element which is complexed by the ligand, as a percentage of the total precursor element in the mixture, such that at least about 80% of the concentration of the radionuclide is complexed by the ligand and less than about 1% of the precursor element is complexed by the ligand. The copper radionuclide complexed to the ligand is separated from the zinc precursor element and released from the ligand by contacting the ligand with an acid to form a copper radionuclide containing eluate. Residual zinc precursor element is removed from the eluate.

DETAILED DESCRIPTION OF THE INVENTION

As used herein, the term precursor element shall include the isotope from which the radionuclide to be recovered is formed and shall additionally include other isotopes of the precursor element which may be present in the starting material along with the isotope from which the radionuclide is formed. The precursor element additionally may include other isotopes of the precursor element which may be formed simultaneously as part of the reaction which produces the radionuclide. For example, for the Zn/Cu system where Cu-64 is recovered following fast neutron capture by 99.9999% pure naturally abundant zinc, the precursor element includes several isotopes known to be present in naturally abundant zinc (Zn-64, Zn-66, Zn-67, Zn-68 and Zn-70) and several additional isotopes (Zn-65, Zn-69m and Zn-71m) formed via thermal neutron reactions (radioactive capture) during bombardment.

The term radionuclide as used herein shall include the particular isotope of the radionuclide sought to be recovered for its utility for radiodiagnostic or other purposes, and any additional isotopes of the element which may be formed simultaneously with the desired isotope. The radionuclide also includes those isotopes of the element of the radionuclide sought to be recovered which may be present in the system as contamination from sources such as reagents, resins, containers and the like. For example, for the Zn/Cu system wherein Cu-64 is recovered following the fast neutron capture by 99.9999% pure naturally abundant zinc, the radionuclide includes the Cu-64, Cu-67 and other copper isotopes which may be produced during the neutron bombardment or which may be present as contamination in process reagents. As to contamination, acids used in connection with this method are known to contain copper contamination in parts-per-million quantities due to the ubiquitous nature of copper.

The proportions of the various isotopes in the precursor element and in the radionuclide differ depending on the nature of the starting material. In the Zn/Cu system where a zinc target is subjected to neutron bombardment, for example, the precursor and radionuclide compositions depend on whether naturally abundant zinc or another target material is used. For example, if isotopically enriched Zn-64, instead of naturally abundant zinc, is used as the target material, the precursor element includes a greater percentage of Zn-64 and a lesser percentage of other zinc isotopes and the radionuclide includes a greater percentage of Cu-64 and a lesser percentage of other Cu isotopes.

A mixture of radionuclide and its precursor element typically contains a low mass of radionuclide such that the mass of precursor element in the mixture is at least two and often several orders of magnitude greater than the mass of the radionuclide in the mixture. In the Zn/Cu system wherein Cu-64 is recovered following fast neutron capture by 99.9999% pure naturally abundant zinc, for example, the mass of precursor element in the mixture is at least about 100 times the mass of radionuclide and typically at least about $10^4$ times the amount of radionuclide. In certain instances the amount of precursor element may be in the range of from at least about $10^4$ to about $10^6$ or more times the amount of radionuclide. The fast neutron capture of Example 1 herein, for example, produced a mixture containing about 0.1 μg copper radionuclide per gram of zinc precursor element in the mixture.

For a Zn/Cu system resulting from a fast neutron capture from which Cu-67 is formed, the precursor element includes Zn-67 and various other zinc isotopes present and the radionuclide includes Cu-67 and any other Cu isotopes present, the composition depending on whether naturally abundant zinc or isotopically enriched zinc is the starting target material. The mass of precursor element in the mixture is typically on the order of at least about $10^4$ times the amount of copper radionuclide, but in practice may be in the range of from at least about $10^4$ to about $10^6$ or more times the amount of copper radionuclide.

For a Zn/Cu system resulting from the decay of Zn-62 into daughter Cu-62, the precursor element includes Zn-62 and various other zinc isotopes and the radionuclide includes Cu-62 and minor amounts of other copper isotopes which may be present as contamination. The mass of precursor element in the mixture, as with the mixtures described above, is typically orders of magnitude greater than the mass of radionuclide in the mixture.

For the Ca/Sc system in which Ca-47 decays into daughter Sc-47, the precursor element includes Ca-47, Ca-46 and additional calcium isotopes. The mass of precursor element is typically on the order of at least about $10^4$ times mass of radionuclide, but in practice may be in a range from at least about $10^4$ to about $5 \times 10^5$ or more times the amount of radionuclide.

In accordance with this method, a solution of the radionuclide and its precursor element is formed in a weak acid, preferably a weak organic acid, most preferably a $C_1$–$C_{10}$ weak organic acid. In the Zn/Cu system described herein, carboxylic acids such as acetic, propionic, formic and lactic acid are particularly preferred. In particular, Zn and Cu metal or compounds of the mixture are dissolved in the weak acid, preferably about 0.5M–2M, most preferably about 1M, acetic acid to provide a weak acid solution containing the radionuclide and precursor element mixture. For Sc radionuclide separation, carboxylic acids such as acetic acid and picolinic acid are preferred.

If the Zn/Cu mixture is of Zn and Cu metals or oxides, the mixture may be dissolved in a strong acid such as nitric, hydrochloric or sulfuric prior to formation of the weak acid solution. This dissolution produces the 2+ oxidation state for both metals. The acid is preferably at least 8M hydrochloric and is most preferably concentrated, that is, 12M. The acid containing the zinc and copper may then be dried to a salt, for example, $ZnCl_2$ and $CuCl_2$, prior to the formation of the weak acid solution. If, however, the radionuclide and precursor element mixture is prepared by irradiation of a salt or other substance such that the mixture is soluble in a weak acid, dissolution in strong acid is not necessary.

The weak acid solution containing the radionuclide and precursor element mixture is contacted with a ligand, generally a chelating ligand, with which the radionuclide is preferentially complexed relative to the precursor element. The ligand is added to a solution having controlled pH containing the radionuclide and precursor element mixture. The ligand and radionuclide thereby form a complex which is separable from the precursor element by, for example, immobilizing the complex on a solid support.

In a preferred embodiment, the ligand is immobilized on a solid support prior to contact with the solution containing the radionuclide and precursor element mixture. The solid support may be glass, a filter, or a resin, but is preferably resin contained in a column. For Zn/Cu systems, a preferred solid support is a styrene based resin such as Chelex resin. Chelex resin, available from Bio-Rad Laboratories (Richmond, Calif.), has iminodiacetate ligands which bind metal ions. Another preferred solid support is 4% beaded agarose resin, available from Sigma Chemical Co. (St. Louis, Missouri).

Upon contact with the radionuclide and precursor element mixture solution, the ligand preferentially forms a complex with the radionuclide relative to the precursor element. The pH of the weak acid solution is closely monitored such that the preference of the particular ligand is sufficient to obtain the desired degree of separation. In particular, the pH of the weak acid solution is preferably in the range of about 2.3 to about 3.1, most preferably about 2.7, for the separation of Cu from Zn using iminodiacetate ligands, tris(carboxymethyl)ethylene diamine or L-aspartic acid as the ligand as described herein.

For the Zn/Cu system, ligands having nitrogen containing functional groups having selectivity for copper, such as iminodiacetate ions of Chelex resin, tris(carboxymethyl) ethylenediamine and L-aspartic acid are preferred. Other suitable ligands for complexing Cu are disclosed in the literature and include Br-benzyl-TETA (BAT) and its related derivatives (Anderson et al., "Copper-64-Labeled Antibodies for PET Imaging", *J. Nucl. Med.* 1992; 33:1685-91), N-propyethylenediamine, its bis(dithiocarbamate), and 8-hydroxyquinoline (Ryan et al. "Comparison of Chelating Agents Immobilized on Glass with Chelex 100 for Removal and Preconcentration of Trace Copper (II)", *Talanta*, Vol. 32, No. 9, pp. 859–863, 1985), phenyl acetic acid (PAA) (Adam et al., "Analytical Use of the Selective Extraction of Copper as its Phenylacetate", *Talanta*, 1972, Vol. 19, pp. 1105–1111), 2,4-dihydroxyacetophenone thiosemicarbazone (DAPT) (Reddy et al., "Sequential Extraction and Determination of Copper and Nickel with 2,4-Dihydroxyacetophenone Thiosemicarbazone", *Talanta*, Vol. 33, No. 7, pp. 617–619, 1986), 3,3',4'-trihydroxyfuchsone-2''-sulphonic acid (Pyrocatechol Violet) (Brajter et al., "Preconcentration and Separation of Metal Ions by Means of Amberlite XAD-2 Loaded with Pyrocatechol Violet", *Talanta*, Vol. 35, No. 1 pp. 65–67, 1988), bis(acetylpivalymethane)-ethylenediimine (Khuhawar et al., "High Performance Liquid Chromatographic Determination of Copper (II) and Nickel (II) by Using Solvent Extraction and Bis-(Acetylpivalylmethane) Ethylenediimine as Complexing Reagent", *Talanta*, Vol. 39, No. 6, pp. 609–612, 1992), methyl isobutyl ketone (Hibbits et al., "The Analysis of Beryllium and Beryllium Oxide-II", *Talanta*, 1960, Vol. 4, pp. 101–103), 1,3-dimethyl-4-imino-5-oximino-alloxan (DAXIM) (Burger, "Analytical Use of 1,3-Dimethyl-4-imino-5-oximino-alloxan-I", *Talanta*, 1961, Vol. 8, pp. 77–84) and N-(dithiocarboxy)sarcosine (DTCS) (Sakai, "Photometric Determination of Copper with N-(Dithiocarboxy)Sarcosine after Preconcentration with Amberlite Xas-2 Resin", *Talanta*, Vol. 27, pp. 1073–1076), among others.

Upon contact of the mixture with the ligand, the percentage of the radionuclide retained by the ligand, as a percentage of the total radionuclide in the mixture, is on the order of at least about 100 times, preferably at least about 1000 times, more preferably at least about 10000 times, the percentage of the precursor element which is complexed by the ligand, as a percentage of the total precursor element in the mixture. Furthermore, the ligand retains a substantial fraction of the total amount of the radionuclide which is in the mixture, preferably at least about 10% of the radionuclide, more preferably at least about 50%, most preferably at least about 90% of the radionuclide. Multiple columns or multiple passes through a single column can be used to separate radionuclide which is not recovered in the first pass.

The radionuclide is eluted from the solid support using an eluant which dissolves the radionuclide to provide an eluate of a radionuclide containing solution.

The eluant is a strong, non-oxidizing acid having a preferred concentration of approximately 1 normal, for example, HCl, HBr, $H_2SO_4$ and $H_3PO_4$. Hydrochloric acid (1M) is the preferred eluant for the Zn/Cu system.

After elution of the radionuclide from the support the radionuclide containing solution may be further purified by anion exchange, solvent extraction or other known methods, if desired. For Zn/Cu or Ca/Sc separation, it is preferred that the eluted radionuclide containing solution is passed over an anion exchange column which selectively retains precursor element in order to separate out residual precursor element. The column volume required is relatively small because the radionuclide containing solution has already been separated from the major quantity of the precursor element. Residual radionuclide retained on the column can be eluted with, for example, 1M HCl. A suitable ion exchange resin for the Zn/Cu and Ca/Sc systems is AG 1-X8 resin available from Bio-Rad (Richmond, Calif.).

The process of the invention permits the separation of micro amounts of radionuclide from relatively large amounts of precursor element without the use of large column volumes and large volumes of reagents. Large column volumes and large volumes of reagents are required with other separation methods in which the relatively large amounts of precursor element are separated out of a radionuclide containing solution by, for example, adsorption on a column. An advantage of the present invention is owed to the fact that the radionuclide is separated from the precursor element and the relative percentage of the radionuclide complexed by the ligand is many times greater than the relative percentage of the precursor element complexed by the ligand. This characteristic of the process is especially advantageous because radionuclides are often generated in micro amounts in mixture with relatively large amounts of precursor element.

As noted above, the radionuclide which is separated from the precursor element includes isotopes in addition to the particular radioisotope sought to be recovered for its utility for radiodiagnostic or other purposes. These additional isotopes dilute the specific activity of the product containing the particular isotope. Because large volumes of reagents are not required in this process, contamination of the radionuclide containing solution and dilution of the final product's specific activity with isotopes contained, for example, in reagents are advantageously minimized.

The following examples further illustrate the invention.

EXAMPLE 1

A column having iminodiacetic functional groups on a styrene based resin (Chelex, Bio-Rad, Richmond, CA) (6 ml bed volume) was prepared by eluting the column sequentially as follows: 20 ml deionized water, 30 ml HCl, 50 ml deionized water, 30 ml 1M NaOH, 50 ml deionized water. The column was then equilibrated with 30 ml of 1M acetic acid (pH=2.7).

Zinc metal targets (99.9999% purity) sealed in evacuated quartz vials which had been neutron irradiated using a steady state nuclear reaction having a U-235 neutron spectrum were provided. Within an average of 4–8 hours from the end of irradiation, the quartz vials were broken and the zinc metal targets (0.653 g each, mean) were dissolved in concentrated HCl. The dissolved targets were transferred to a teflon beaker and evaporated to dryness on a hot plate. The resulting dried zinc and copper chlorides were dissolved in 3 ml of 1M acetic acid to produce a solution containing the Zn/Cu mixture having a pH of about 2.7. The solution containing the Zn/Cu mixture was contacted with the Chelex column. The Cu-64 (and Cu-67 minor constituent) was selectively retained on the column while the Zn passed through. The column was washed with 15 ml of 1M acetic acid and rinsed with 3 ml deionized water to remove excess solution and zinc which may have been retained. The Cu-64 was eluted from the Chelex column with approximately 10 ml of 1M HCl. The flow rate of solution through the column during each elution was increased by application of pressure to the top of the column using a syringe and stopper attachment. The total time from first contact of the mixture with the column to final elution was approximately 10–15 minutes.

An anion column (AG 1-X8 resin available from Bio-Rad, Richmond, Calif.) having a bed volume of 6 ml was prepared by washing with 30 ml of 6M HCl and equilibrating with 1M HCl. The eluate containing the Cu-64 was contacted with the anion exchange column which selectively retained Zn which had been retained on the Chelex column with the Cu-64. The Cu-64 passed through the anion exchange column. The anion exchange column was eluted with 10 ml of 1M HCl to elute any remaining Cu-64.

The final Cu-64 activity was determined using a dose calibrator (Atomlab 100, Atomic Products Corporation, Shirley, N.Y. or Capintec, Inc., Model CRC-10) and aliquots were analyzed by high resolution gamma ray spectroscopy to determine radio-purity. The analysis used a germanium detector coupled to a ND-9900 gamma-ray spectroscopy system (Canberra Inds., Inc., Meriden, Conn.). The established geometry was calibrated for absolute efficiency with a mixed gamma-ray standard (Analytics, Inc., Atlanta, Ga.) traceable to the National Institutes of Science and Technology. Cu-64 aliquots (5–10 mCi) were saved for Cu analysis and, following decay of Cu-64 and Cu-67, were counted in a gamma counter (NaI thru-hole detector, Auto-Gamma 5000 series, Packard Instrument Co., Meriden, Conn.). The residual Zn-65 activity was thereby determined in order to calculate the Zn purification factor, defined as the ratio of the Zn-65 in the final Cu-64 product divided by the total Zn-65 produced. The total Zn-65 activity was measured with a dose calibrator.

The separation described in this example was carried out in a glove box equipped with charcoal and HEPA exhaust filters. Personnel radiation monitors included ring monitors and a body dosimeter. The separation was monitored by a health physics technician. Care was take to minimize radiation dose by use of lead shielding, and radioactive samples were handled at a distance using thongs.

Twenty-four runs of the procedure of this example resulted in a mean Cu-64 recovery of 257 mCi (standard error of the mean (SEM)=±8.9 mCi) at the end of neutron irradiation, with the mean Cu-64 activity recovered being 0.393 mCi/mg Zn irradiated (SEM=±0.007 mCi). Radio-purity of the Cu-64 was determined using high resolution gamma-ray spectroscopy after separation. No radio-impurities other than Cu-67 were detected. The Cu-67 impurity level was approximately 1.4 µCi per mCi of Cu-64 at the end of neutron irradiation.

After irradiation, but prior to separation, each Zn target sample (0.653 g average) contained the following approximate radioactivities: Zn-65, 18 mCi; Zn-69 m, 33 mCi; and Zn-71, less than 1 mCi. The Zn-65 impurity content in the final product averaged 6.3 pCi per mCi of Cu-64 at the end of neutron irradiation. The Zn purification factor had a mean of $8.5 \times 10^{-8}$. The separation removed 99.9999915% of the Zn-65 produced.

EXAMPLE 2

A Chelex column was prepared as described in Example 1. Two quartz vials containing 1.4 g of high purity Zn metal were neutron irradiated and broken, and Cu-64 separation was conducted as described in Example 1. 532 mCi of Cu-64 was recovered, decay corrected to account for the time lapsed since the end of irradiation. The Zn purification factor was determined as in Example 1 and, for the overall separation including both columns, was determined to be $6.7 \times 10^{-7}$. The Zn purification factor for the Chelex column alone was determined to be $5.1 \times 10^{-3}$.

EXAMPLE 3

A Chelex column (6 ml bed volume) was prepared as described in Example 1. Zinc metal (20.3 grams) and copper metal (20 micrograms) were dissolved in 120 ml concentrated HCl by adding a portion of the acid thereto, allowing a portion of the zinc to dissolve, pouring the solution off, and repeating until the entire sample was dissolved. Zinc-65 (7.8 mCi) and Cu-67 ($9.3 \times 10^{-2}$ μCi) were added as tracers together with Ca-47 ($2.1 \times 10^{-2}$ μCi) and Sc-47 ($5.9 \times 10^{-2}$ μCi). The dissolved mixture was transferred to a teflon beaker and evaporated to dryness on a hot plate. The resulting dried salt was dissolved in 60 ml of 1M acetic acid to yield a solution having a pH of 2.7. The solution containing the mixture was contacted with the Chelex column, which was then eluted with 75 ml of 1M acetic acid. The Cu and Sc were then eluted from the column with 25.4 ml 1M HCl to provide an eluate containing Cu-64 and Sc-47.

An anion column (AG 1-X8 resin available from Bio-Rad) having a bed volume of 6 ml was prepared by washing with 30 ml of 6M HCl and equilibrating with 1M HCl. The solution containing the Cu-64 and Sc-47 was contacted with the anion exchange column which selectively retained Zn which had been retained on the Chelex column with the Cu-64. The Cu-64 and Sc-47 passed through the anion exchange column. The anion exchange column was eluted with 10 ml of 1M HCl into a calibration vial to elute any remaining Cu-64.

The final Cu-64 activity and residual Zn-65 activity were determined using a dose calibrator and aliquots were analyzed by high resolution gamma ray spectroscopy to determine radio-purity as described in Example 1. The Zn purification factor was determined to be $1.5 \times 10^{-8}$ and the Cu recovery was determined to be 65.4%. The anion column retained 16.6 μCi of Zn-65 (of 7.8 mCi) indicating that this amount had been retained on the Chelex column with the Cu-67. The Zn purification factor using the Chelex column alone was determined to be $3.3 \times 10^{-3}$.

The Ca purification factor was determined to be $3.9 \times 10^{-3}$, with 79.6% of the Sc-47 activity recovered in the final fraction.

EXAMPLE 4

A Chelex column (6 ml bed volume) was prepared as described in Example 1. Zinc metal (20.5 grams) was dissolved in 120 ml concentrated HCl by adding a portion of the acid thereto, allowing a portion of the zinc to dissolve, pouring the solution off, and repeating until the entire sample was dissolved. Zinc-65 (6.3 mCi) and Cu-67 (11 μCi) were added as tracers. The dissolved mixture was transferred to a teflon beaker and evaporated to dryness on a hot plate. The resulting dried salt was dissolved in 60 ml of 1M acetic acid to yield a solution having a pH of 2.7. The solution containing the mixture was contacted with the Chelex column, which was then eluted with 75 ml of 1M acetic acid, pH 2.7. The Cu was then eluted from the column with 10 ml 1M HCl to provide a Cu containing eluate.

The Cu containing solution was further purified as described in Example 3. The Zn purification factor was determined to be $1.39 \times 10^{-7}$ and the Cu recovery was determined to be 100%. The anion column retained 24.9 μCi of Zn-65 (of 6.3 mCi) indicating that this amount had been retained on the Chelex column with the Cu-67. The Zn purification factor using the Chelex column alone was determined to be $3.9 \times 10^{-3}$.

EXAMPLE 5

A Chelex column (2 ml bed volume) was prepared as described in Example 1. Zinc (0.288 g) was dissolved in 4 ml concentrated HNO₃. Zinc-65 (0.270 mCi) and Cu-64 (33.2 μCi) were added. The dissolved mixture was transferred to a teflon beaker and evaporated to dryness on a hot plate. The resulting dried zinc and copper nitrates were in 5 ml of 1M acetic acid to yield a solution having a pH of 2.7. The solution containing the Zn/Cu mixture was contacted with the Chelex column and as described in Example 1. The Cu was then eluted from the column with 10 ml 1M HCl directly into a 10 ml scintillation vial. The Cu containing solution was analyzed as in Example 1. The Zn purification factor was determined to be $8.8 \times 10^{-2}$ and the Cu recovery was determined to be 100%.

EXAMPLE 6

A Chelex column (2 ml bed volume) was prepared as described in Example 1, with the exception that the final rinse of the column was with 0.1M propionic acid. Zn (0.222 g) was dissolved in 4 ml concentrated HCl. Zinc-65 (0.270 mCi) and Cu-64 (33.2 μCi) were added. The dissolved mixture was transferred to a teflon beaker and evaporated to dryness on a hot plate. The resulting dried zinc and copper chloride were dissolved in 5 ml of 0.1M propionic acid to yield a solution having a pH of 2.7. The solution containing the Zn/Cu mixture was contacted with the Chelex column. The column was washed with 15 ml of 0.1M propionic acid and rinsed with 3 ml deionized water to remove excess solution and zinc which may have been retained. The Cu-64 was eluted from the Chelex column with approximately 10 ml of 1M HCl directly into a 10 ml scintillation vial. The Cu containing solution was analyzed as in Example 1. The Zn purification factor was determined to be $2.5 \times 10^{-2}$ and the Cu recovery was determined to be 93.3%.

EXAMPLE 7

A Chelex column (2 ml bed volume) was prepared as described in Example 1, with the exception that the final rinse of the column was with 0.1M formic acid. Zinc (0.250 g) was dissolved in 4 ml concentrated HCl. Zinc-65 (0.270 mCi), Cu-64 (33.2 μCi), Ca-47 ($1.02 \times 10^{-2}$ μCi) and Sc-47 ($1.1 \times 10^{-2}$ μCi) were added. The dissolved mixture was transferred to a teflon beaker and evaporated to dryness on a hot plate. The resulting dried zinc and copper chloride were dissolved in 5 ml of 0.1M formic acid to yield a solution having a pH of 2.7. The solution containing the mixture was contacted with the Chelex column. The column was washed with 15 ml of 0.1M formic acid and rinsed with 3 ml deionized water to remove excess solution and zinc which may have been retained. The Cu-64 was eluted from the Chelex column with approximately 10 ml of 1M HCl directly into a 10 ml scintillation vial. The Cu containing solution was analyzed as in Example 1. The Zn purification factor was determined to be $3.1 \times 10^{-2}$ and the Cu recovery was determined to be 100%. The Ca purification factor was determined to be $6.5 \times 10^{-3}$ and the Sc recovery determined to be 90%.

EXAMPLE 8

A Chelex column (2 ml bed volume) was prepared as described in Example 1, with the exception that the final rinse of the column was with 0.1 M lactic acid. Zinc (0.251 g) was dissolved in concentrated HCl. Zinc-65 (0.279 mCi) and Cu-64 (33.2 µCi) were added. The dissolved mixture was transferred to a teflon beaker and evaporated to dryness on a hot plate. The resulting dried zinc and copper chloride were dissolved in 5 ml of 0.1M lactic acid to yield a solution having a pH of 2.7. The solution containing the mixture was contacted with the Chelex column. The column was washed with 15 ml of 0.1M lactic acid and rinsed with 3 ml deionized water to remove excess solution and zinc which may have been retained. The Cu was then eluted from the column with 10 ml 1M HCl directly into a 10 ml scintillation vial. The Cu containing solution was analyzed as in Example 1. The Zn purification factor was determined to be $1.3 \times 10^{-2}$ and the Cu recovery was determined to be 100%.

EXAMPLE 9

A column of tris(carboxymethyl)ethylene diamine insolubilized on a 4% beaded agarose resin (0.3 ml bed volume) was prepared by equilibrating with 30 ml of 1M acetic acid (2.7 pH).

Zn (0.267 g) was dissolved in 4 ml concentrated HCl. Zinc-65 (0.270 mCi) and Cu-64 (33.2 µCi) were added. The dissolved mixture was transferred to a teflon beaker and evaporated to dryness on a hot plate. The resulting dried zinc and copper chloride were dissolved in 5 ml of 1M acetic acid to yield a solution having a pH of 2.7. The solution containing the Zn/Cu mixture was contacted with the Chelex column and as described in Example 1. The Cu was then eluted from the column with 10 ml 1M HCl directly into a 10 ml scintillation vial. The Cu containing solution was analyzed as in Example 1. The Zn purification factor was determined to be $4 \times 10^{-4}$ and the Cu recovery was determined to be 100%.

EXAMPLE 10

A column of L-aspartic acid insolubilized on a 4% beaded agarose resin (1 ml bed volume) was prepared by eluting the column with 30 ml of 1M acetic acid (2.7 pH).

Zn (0.281 g) was dissolved in 4 ml concentrated HCl. Zinc-65 (0.270 mCi) and Cu-64 (33.2 µCi) were added. The dissolved mixture was transferred to a teflon beaker and evaporated to dryness on a hot plate. The resulting dried zinc and copper chloride were dissolved in 5 ml of 1M acetic acid to yield a solution having a pH of 2.7. The solution containing the Zn/Cu mixture was contacted with the Chelex column and as described in Example 1. The Cu was then eluted from the column with 10 ml 1M HCl directly into a 10 ml calibrated scintillation vial. The Cu containing solution was analyzed as in Example 1. The Zn purification factor was determined to be $2.2 \times 10^{-6}$ and the Cu recovery was determined to be 11.8%.

EXAMPLE 11

A Chelex column (2 ml bed volume) was prepared as described in Example 1, with the exception that the final rinse of the column was with 0.1M picolinic acid (pH 2.7). Zn (0.257 g) was dissolved in 4 ml concentrated HCl. Zinc-65 (0.270 mCi) and Cu64 (33.2 µCi) were added as tracers together with Ca-47 ($1.02 \times 10^{-2}$ µCi) and Sc-47 ($1.1 \times 10^{-2}$ µCi). The dissolved mixture was transferred to a teflon beaker and evaporated to dryness on a hot plate. The resulting dried zinc and copper chloride were dissolved in 5 ml of 0.1M picolinic acid to yield a solution having a pH of 2.7. The solution containing the mixture was contacted with the Chelex column. The column was washed with 30 ml of 0.1M picolinic and rinsed with 3 ml deionized water to remove excess solution and zinc which may have been retained. The Cu was eluted from the Chelex column with approximately 10 ml of 1M HCl directly into a 10 ml calibrated scintillation vial. The Cu containing solution was analyzed as in Example 1. The Ca purification factor was determined to be $2.5 \times 10^{-3}$ and the Sc recovery was determined to be 100%. The Cu-64 and Zn-65 were not retained on tile Chelex column, and therefore were not present in solution.

In Examples 5–11, the copper was added as 0.01 ml of stock Cu-64 solution containing 190.4 µCi of Cu-64 and 0.2 µCi of Cu-67, as corrected to the end of irradiation. Assuming a specific activity of 564,000 µCi/µg Cu at the end of irradiation, the copper mass was approximately $3.4 \times 10^{-10}$g. The mass of zinc used in Examples 5×11 was approximately 0.25 g having about 270 µCi of Zn-65 activity. The zinc mass was therefore approximately $7 \times 10^8$ greater than the copper mass for each example. In Examples 7 and 11, the calcium was added as 0.01 ml of stock Ca-47 solution containing 0.0101 µCi of Ca-47 in equilibrium with 0.011 µCi of Sc-47, as corrected to the start of the experiments. The Ca-47 had a known specific activity of 1.49 µCi/µg Ca, as corrected to the start of the experiments. The calcium mass was therefore approximately $7 \times 10^{-9}$g. The mass of scandium used in Examples 7 and 11 was approximately $1.35 \times 10^5$ g. The calcium mass was therefore approximately $5.2 \times 10^5$ greater than the scandium mass for these example. Accordingly, it can be seen that the method of the invention is effective for recovering micro amounts of radionuclide from much greater quantities of precursor element.

The separations described in the above examples were achieved in about two hours per separation. This is a substantially shorter time period than is associated with radionuclide separation using previous methods. This savings of time advantageously reduces personnel costs, radiation exposure and loss of activity of the radionuclide during the separation due to decay.

It should also be noted that this invention includes the separation of radionuclides from precursor elements other than in the Zn/Cu system. The process has proven to be particularly effective for separating a radionuclide from a precursor element where the difference between the atomic number of the radionuclide and precursor element is no more than three. The applicability of the process outside the Zn/Cu system has been proven by the successful separation of Sc radionuclide from Ca precursor element described in the examples herein. Copper is given primary consideration in the foregoing description due to the current interest in using Cu-64 for PET. It is within the skill of the art to find suitable ligands and acids and otherwise optimize the invention for separating radionuclides other than copper and for separating copper from precursor elements other than zinc, as the case may be.

As various changes could be made in the above embodiments without departing from the scope of the invention, it is intended that all matter contained in the above description shall be interpreted as illustrative and not in a limiting sense.

It is claimed:

1. A process for separating a radionuclide from a mixture containing the radionuclide and a precursor element of the radionuclide in which the mass of the precursor element is at least about 100 times the mass of the radionuclide, comprising:
   (a) preparing a weak acid solution which contains the mixture of the radionuclide and the element,
   (b) contacting the solution with a ligand which preferentially forms a complex with the radionuclide relative to the precursor element, the percentage of the radionuclide which is complexed by the ligand, as a percentage of the total radionuclide in the mixture, being on the order of at least about 100 times the percentage of the precursor element which is complexed by the ligand, as a percentage of the total precursor element in the mixture,
   (c) separating the radionuclide complexed to the ligand from the precursor element, and
   (d) releasing the radionuclide from the ligand.

2. The process of claim 1 wherein the percentage of the radionuclide which is complexed by the ligand, as a percentage of the total radionuclide in the mixture, is on the order of at least about 1000 times the percentage of the precursor element which is complexed by the ligand, as a percentage of the total precursor element in the mixture.

3. The process of claim 2 wherein at least about 80% of the concentration of the radionuclide is complexed by the ligand and less than about 1% of the precursor element is complexed by the ligand.

4. The process of claim 3 wherein the radionuclide is copper and the precursor element is zinc.

5. The process of claim 3 wherein the radionuclide is scandium and the precursor element is calcium.

6. The process of claim 3 wherein the weak acid is selected from the group consisting of acetic, propionic, picolinic, lactic and formic acids.

7. The process of claim 3 wherein the ligand is immobilized on a solid support.

8. A process for separating a copper radionuclide from a mixture containing the copper radionuclide and a zinc precursor element of the copper radionuclide in which the mass of the zinc precursor element is at least about 100 times the mass of the copper radionuclide, comprising:
   (a) preparing a weak acid solution which contains the mixture of the copper radionuclide and the zinc precursor element,
   (b) contacting the solution with a ligand which preferentially forms a complex with the copper radionuclide relative to the zinc precursor element, the percentage of the radionuclide which is complexed by the ligand, as a percentage of the total radionuclide in the mixture, being on the order of at least about 100 times the percentage of the precursor element which is complexed by the ligand, as a percentage of the total precursor element in the mixture,
   (c) separating the copper radionuclide complexed to the ligand from the zinc precursor element, and
   (d) releasing the copper radionuclide from the ligand.

9. The process of claim 8 comprising dissolving solid zinc and copper with a strong acid prior to forming said solution in weak acid.

10. The process of claim 9 wherein the strong acid is hydrochloric, nitric or sulfuric acid.

11. The process of claim 8 wherein the weak acid is selected from the group consisting of acetic acid, propionic acid, formic acid and lactic acid.

12. The process of claim 8 wherein the pH of the weak acid solution is between about 2.3 and about 3.1.

13. The process of claim 12 wherein the pH of the weak acid solution is about 2.7.

14. The process of claim 8 wherein the ligand is immobilized on a solid support.

15. The process of claim 14 wherein iminodiacetate ions immobilized on a styrene based resin constitutes the ligand immobilized on the solid support.

16. The process of claim 8 wherein the ligand is selected from the group consisting of tris(carboxymethyl)ethylene diamine and L-aspartic acid.

17. The process of claim 8 comprising contacting the ligand with an acid to form a copper radionuclide containing eluate, and
   contacting the copper containing eluate with an anion exchange column which preferentially retains zinc ions over copper ions.

18. The process of claim 8 comprising forming the mixture of copper radionuclide and zinc precursor element by fast neutron reaction irradiation of a zinc target.

19. The process of claim 14 wherein the solid support is a resin contained in a column.

20. A process for producing a radionuclide adapted for radiation therapy or diagnosis of a mammal by separating a copper radionuclide from a mixture of copper radionuclide and a zinc precursor element comprising:
   (a) forming a solution in weak acid which contains the mixture of copper radionuclide and zinc precursor element, said copper radionuclide resulting from fast neutron capture by a zinc target, said solution having a pH in the range of about 2.3 to 3.1,
   (b) contacting the solution with a ligand immobilized on a resin, which ligand preferentially forms a complex with the copper radionuclide relative to the zinc precursor element, the percentage of the radionuclide which is complexed by the ligand, as a percentage of the total radionuclide in the mixture, being on the order of at least about 100 times the percentage of the precursor element which is complexed by tile ligand, as a percentage of the total precursor element in the mixture, such that at least about 80% of the concentration of the radionuclide is complexed by the ligand and less than about 1% of the precursor element is complexed by the ligand,
   (c) separating the copper radionuclide complexed to the ligand from the zinc precursor element, and
   (d) releasing the copper radionuclide from the ligand by contacting the ligand with an acid to form a copper radionuclide containing eluate, and
   (e) removing residual zinc precursor element from the eluate.

* * * * *